Figure 1:
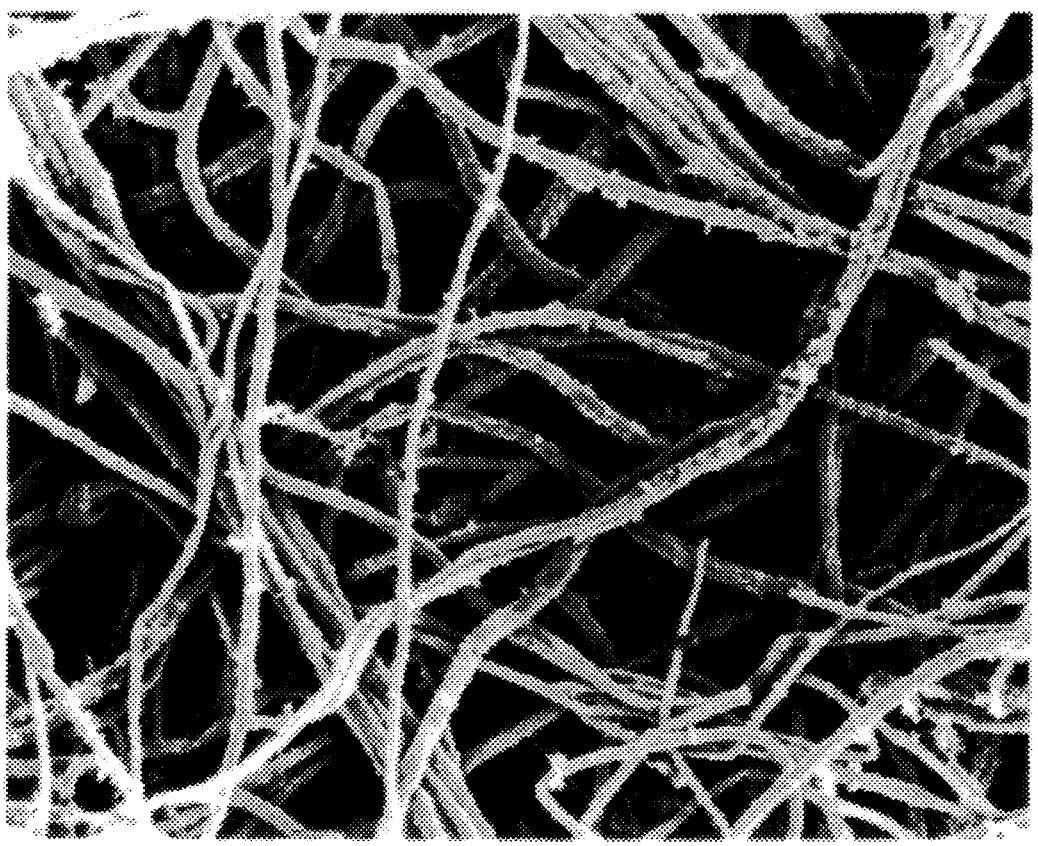

United States Patent [19]

Strobel et al.

[11] Patent Number: 5,648,376

[45] Date of Patent: Jul. 15, 1997

[54] IMMUNOSUPPRESSANT DITERPENE COMPOUND

[75] Inventors: Gary A. Strobel, Bozeman, Mont.; Nathan B. Pliam, Palo Alto, Calif.

[73] Assignee: Pharmagenesis, Inc., Palo Alto, Calif.

[21] Appl. No.: 375,362

[22] Filed: Jan. 19, 1995

[51] Int. Cl.$^6$ .......... A61K 31/35; A61K 31/34; C12P 17/06; C07D 407/00
[52] U.S. Cl. .......... 514/451; 435/125; 435/126; 514/461; 514/468; 549/414; 549/433
[58] Field of Search .......... 514/453, 449, 514/451, 454; 435/125; 549/273, 414, 433

[56] References Cited

U.S. PATENT DOCUMENTS 5,294,443  3/1994  Lipsky et al. .......... 424/195.1
5,430,054  7/1995  Qian et al. .......... 514/468

OTHER PUBLICATIONS

Zheng, et al., Zhongguo Xixue Kexueyuan Xuebao (1994), 16(1), 24–8.
Zheng, et al., Zhongguo Xixue Kexueyuan Xuebao (1991), 13(6), 391–7.

Primary Examiner—David M. Naff
Attorney, Agent, or Firm—Peter J. Dehlinger; Vincent M. Powers; LeeAnn Gorthey

[57] ABSTRACT

An immunosuppressant compound is produced having the structure:

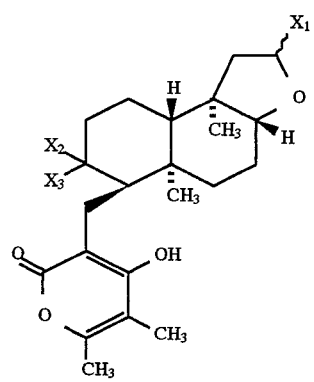

or a mirror image thereof, wherein $X_1$ is 2,2-dimethylvinyl and $X_2$ and $X_3$ together are $=CH_2$; or $X_1$ is 2,2-dimethyloxiranyl, and $X_2$ and $X_3$ together are $-O-CH_2-$; or $X_1$ is 1,2-dihydroxy-2-methyl-propyl, $X_2$ is $-CH_2OH$, and $X_3$ is OH; or $X_1$ is 2-hydroxy-2-methylpropyl, $X_2$ is H, and $X_3$ is $CH_2OH$; or $X_1$ is COOR, and $X_2$ and $X_3$ together are $=O$, where R is a lower alkyl, phenyl, or benzyl group; or $X_1$ is 2-methylpropyl, $X_2$ is H, and $X_3$ is $CH_3$. The compound can be produced by culturing *Fusarium subglutinans f. sp. tripterygii* ATCC 74358 isolated from the stems of *Tripterygium wilfordii*. A pharmaceutical composition for immunosuppression therapy is prepared containing the compound and a pharmaceutically acceptable vehicle.

11 Claims, 12 Drawing Sheets

IMMUNOSUPPRESSANT DITERPENE COMPOUND

FIELD OF THE INVENTION

The present invention relates to a novel diterpene compound with immunosuppressive activity, and to a method of producing the compound using a fungal organism.

References

Boyum, A., *Scan. J. Lab Invest.* 21:77 (1968).
Chen, K. et al., *J. Nat. Prod.* 55(3):340 (1992).
Deng, F., et al., *Acta Pharm. Sin.* 27:867 (1992).
Green, L.M., et al., *J. Immunol. Meth.* 70:257–286 (1984).
Gunstone, *Adv. Org. Chem.* 1:103 (1962).
Guo, J., et al., *Chin. Med. J.* 94(7):405 (1981).
Ma, P.-C., et al., *Yaoxue Xuebao* 26(10):759 (1991a).
Ma, P.-C., et al., *Zhiwu Xuebao* 33(5):370 (1991b).
Ma, P.-C., et al., *J. Chin. Pharm. Sci.* 1 (2):12 (1992a).
Ma, P.-C., et al., *Zhongguo Yaoke Daxue Xuebao* 23 (5):297 (1992b).
Mishell, B., et al., Eds., *Selected Methods in Cellular Immunology*, Freeman and Co. (1980).
O'Gara, A., and Defrance, T., "Bioassays for interleukins", In *Laboratory Methods in Immunology* (Zola, H., Ed.) CRC Press (1990).
Paquette, L. A., and Barret, J. H., *J. Org. Chem.* 32:1363 (1967).
Paquette, L. A., and Barrett, J. H., *Organic Synthesis, Collective Volume* 5:467 (1973).
Pinkerton, F., and Strobel, G. A., *Proc. Natl. Acad. Sci.* 73:4007–4011 (1976).
Rocek and Westheimer, *J. Am. Chem. Soc.* 84:2241 (1962).
Sebek, O.K., *Mycologia* 75:383 (1983).
Shen, J., et al., *Chin. Chem. Lett.* 3(2):113 (1992).
Shishido, K., et al., *Tetrahedron Lett.* 34(2):339 (1993).
Swern, et al., *J. Am. Chem. Soc.* 68:6504 (1946).
Takaishi, Y., et al., *Phytochem.* 29:3869 (1990).
Takaishi, Y., et al., *Phytochem.* 30(5):1561 (1991a).
Takaishi, Y., et al., *Phytochem.* 30(5):1567 (1991b).
Takaishi, Y., et al., *Phytochem.* 30(9):3027 (1991c).
Takaishi, Y., et al., *PCT Publication No.* WO 91/13855 (1991d).
Takaishi, Y., et al., *Phytochem.* 31(11):3943 (1992a).
Takaishi, Y., et al., *Tetrahedron Lett.* 33:7177 (1992b).
Turner, W. B., *The Filamentous Fungi*, Vol. 1, (Smith, J. E., et al., Eds.) Edward Arnold Pub., London, pp. 122–139 (1975).
Wiberg, et al., *Adv. Org. Chem.* 1:103 (1960).
Wu, Q., et al., *Jiegou Huaxue* 11(1):55 (1992).
Ya, L., et al., *Can. Chem.* 68(3):371 (1990).
Ya, L., et al., *Phytochem.* 30(2):719 (1991).
Zhang, W., et al., *Acta Pharm. Sin.* 21:592 (1986a).
Zhang, L., et al., *Zhongguo Yaoli Xuebao* 7:85 (1986b).
Zhang, L., et al., *Acta Pharma. Sinica* 25(8):573 (1990a).
Zhang, L., et al., *Planta Med.*, 56(1):98 (1990b).
Zhang, D. M., et al, *Yaoxue Xuebao* 27:638 (1992).
Zheng, J., et al., *Zhongguo Yixue Kexueyuan Xuebao*, 13(6):391 (1991).

BACKGROUND OF THE INVENTION

Many useful pharmaceutical agents are derived from plants. In some cases, the plant-derived compound provides a drug lead which is then chemically modified to improve its pharmacological activity and/or simplify its structure for chemical synthesis. In many cases, e.g., where the plant-derived compound is a complex structure, chemical synthesis is impractical, and the compound must be obtained by direct extraction from plants. If the plant is in short supply, or a complex purification scheme is required, or the yield is low, direct extraction from plants may not be practical.

Production of pharmaceutical agents using plant cell cultures has been reported for only a few cases. In general, obtaining what are usually complex compounds by this approach has not been feasible to date.

One plant which illustrates the potential for plant secondary metabolites as useful pharmaceutical agents, and also the difficulty of producing the plant products in practical yields, is *Tripterygium wilfordii* (TW). A number of compounds having immunosuppressive or other activities have been isolated from extracts of root tissues from TW, including tripterinin (PCT Application PCT/US94/02540), 16-hydroxytriptolide (Ma, 1991a; 1992a), triptriolide (Ma, 1991b), celastrol (Zhang, 1986a,b), tripchlorolide (Zhang, 1992), triptophenolide (Deng, 1992), triptonide (Wu, 1992), tripterine (Zhang, 1990a), tripterygic acid (Zhang, 1990b), sesquiterpene alkaloids (Ya, 1990), isowilfordine (Ya, 1991), sesquiterpene esters (Takaishi, 1990; 1991a; 1992a), sesquiterpene polyol esters (Takaishi, 1991b,c), phenanthrene derivatives (Takaishi, 1991d) tripterygone (Zhang, 1991), salaspermic acid (Chen, 1992), other diterpene lactone epoxide compounds (Zheng, 1991; Ma, 1992b), and diterpene quinones (Shen, 1992; Takaishi, 1992b; Shishido, 1993).

However, in most cases, these compounds are structurally complex molecules which are difficult to purify in useful quantities from plants, and difficult or impossible to synthesize in practical yields. At present, it is not known whether cultured cells from *T. wilfordii* could be induced to produce any of these compounds in commercially useful amounts.

It would therefore be of significant benefit to provide a method for producing complex plant terpenoids, and in particular, terpenoid immunosuppressant compounds by methods which overcome the limitations noted above. At the same time it would be advantageous to discover additional plant-derived compounds, or mimics thereof, with therapeutically useful properties.

SUMMARY OF THE INVENTION

The invention includes, in one aspect, a novel immunosuppressant compound, having the structure:

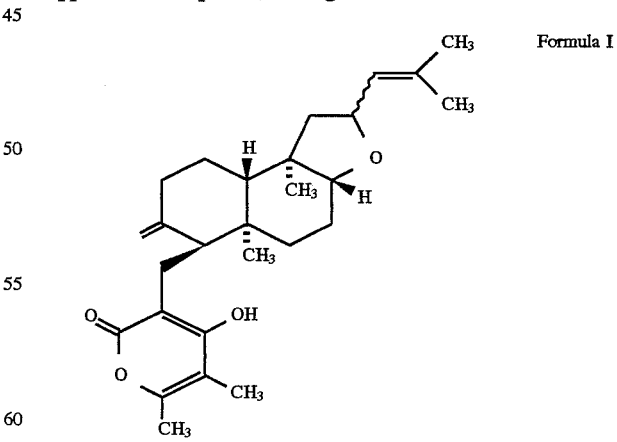

Formula I

The compound, which is referred to herein as subglutinol, may consist essentially of the 12-(R) stereoisomer or the 12-(S) stereoisomer, or a mixture of the two. The compound can also be produced in a form radiolabeled with $^{14}C$.

More generally, the compound of the invention has the form:

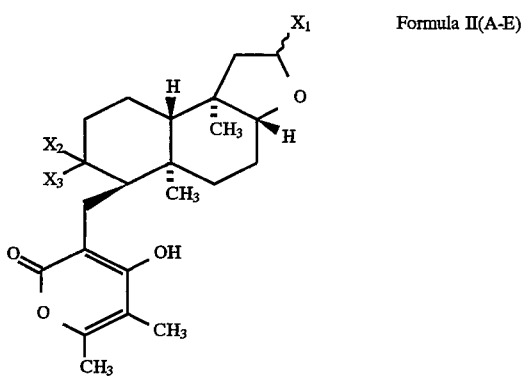

Formula II(A-E)

where $X_1$ is 2,2-dimethylvinyl and $X_2$ and $X_3$ together are $=CH_2$; or $X_1$ is 2,2-dimethyloxiranyl, and $X_2$ and $X_3$ together are $—O—CH_2—$; or $X_1$ is 1,2-dihydroxy-2-methylpropyl, $X_2$ is $—CH_2OH$, and $X_3$ is OH; or $X_1$ is 2-hydroxy-2-methylpropyl, $X_2$ is OH, and $X_3$ is $CH_2OH$; or $X_1$ is 2-methylpropyl, $X_2$ is H, and $X_3$ is $CH_3$; or $X_1$ is COOR, and $X_2$ and $X_3$ together are $=O$, where R is a lower alkyl, phenyl, or benzyl group.

In a related aspect, the invention includes a pharmaceutical composition for use in immunosuppressant therapy. The composition includes a compound of the type described above, in a pharmaceutically acceptable vehicle.

In still another aspect, the invention includes a method for producing a Tripterygium wilfordii secondary metabolite (or a mimic of such a secondary metabolite) having immunosuppressive activity. The method includes culturing, in a culture medium effective to support fungal cell growth, a Fusarium subglutinans fungal organism derived from a Tripterygium wilfordii plant, and isolating the compound from the culture medium. In one general embodiment, the compound is a diterpene, as exemplified by the above subglutinol compound.

Also forming part of the invention is a fungal organism, in substantially pure form, capable of producing a *Tripterygium wilfordii* secondary metabolite compound (or a mimic of such a secondary metabolite) having immunosuppressive activity. The organism is *Fusarium subglutinans f.sp. tripterygii*, i.e., a strain or isolate of *F. subglutinans* obtained from the *Tripterygium wilfordii* plant, e.g., the stem of the plant. The organism is exemplified by the *F. subglutinans* strain identified as TW200 deposit in the EcoPharm Collection, and on deposit with the ATCC under accession number ATCC 74358. The compound produced is preferably a diterpene immunosuppressant, as exemplified by the above subglutinol compound.

These and other objects and features of the invention will become more fully apparent when the following detailed description of the invention is read in conjunction with the accompanying drawings.

BRIEF DESCRIPTION OF THE DRAWINGS

FIG. 1 is an electron micrograph of an isolated *F. subglutinans f.sp. tripterygii* endophyte used in a method of the invention;

FIG. 2 is a high pressure liquid chromatography (HPLC) profile of a partially purified ethyl acetate extract from *F. subglutinans f.sp. tripterygii*, showing the elution positions of subglutinol A and subglutinol B;

FIG. 3 shows ultraviolet (UV) absorption spectra of subglutinol A and subglutinol B (solid line, dashed line);

FIG. 4 shows an infrared (IR) spectrum of subglutinol A;

FIG. 5 shows a $^{13}C$-nuclear magnetic resonance (NMR) spectrum (100 MHz) of subglutinol A;

FIG. 6A and 6B show $^{1}H$-NMR spectra (500 MHz) of subglutinol A and subglutinol B, respectively;

FIGS. 7A and 7B show mass spectra of subglutinol A and subglutinol B, respectively.

FIGS. 8A and 8B show proposed chemical structures for subglutinol A and subglutinol B, respectively;

FIGS. 9A–9E show structures for five subglutinol analogs;

FIGS. 10–12 show plots of percent suppression of proliferation of peripheral blood lymphocytes (PBLs) (FIG. 10), percent inhibition of interleukin-1 (IL-1) action on mouse thymocytes (FIG. 11), and percent suppression of proliferation of lymphocytes in a mixed lymphocyte reaction (FIG. 12), as a function of subglutinol concentration.

DETAILED DESCRIPTION OF THE INVENTION

I. Definitions

"Immunosuppressant" compound refers to a compound capable of inhibiting the normal immune response in a mammalian subject, as indicated by the ability to suppress proliferation of stimulated peripheral blood lymphocytes (PBLs); the ability to inhibit IL-1 or IL-2-induced proliferation of thymocytes; or the ability to inhibit production of IL-1, IL-2, IL-6, or TNFα by PBLs. Immunosuppressive effects include the ability to suppress an autoimmune response, deterrence against transplant rejection and suppression of graft-versus-host disease.

"*Fusarium subglutinans f.sp. tripterygii*" refers to a fungus obtainable from a *Tripterygium wilfordii* plant, e.g., from the plant stem, and having the following characteristics:

1. No chlamydospores are present;
2. Microconidia are abundant, oval and usually single-celled, and not produced in chains; microconidia are produced only in false heads;
3. Macroconidia are abundant, only slightly sickle shaped to almost straight with the dorsal and ventral surfaces almost parallel, and with thin delicate walls; the basal cell is foot shaped; and
4. Conidophores are unbranched.

An exemplary isolate of *Fusarium subglutinans f.sp. tripterygii* is the isolate identified as TW200 deposited in the EcoPharm Collection, EcoPharm, 900 Technology Dr. #C, Bozeman, M T, 59715, and which was deposited on Jan. 11, 1996 with the American Type Culture Collection (ATCC), 12301 Parklawn Drive, Rockville, Md. 20852, under accession number ATCC 74358.

"Secondary metabolite" refers to a biosynthetic product produced by a fungus which is not absolutely required for fungal growth or viability, i.e., for protein synthesis, transcription, DNA replication, or the like (Sebek, 1983; Turner, 1975). Examples of compounds which have been designated as secondary metabolites include antibiotics such as penicillin, ergot alkaloids, cyclosporin, and gibberellins (Wainwright, 1992). For the present invention, "secondary metabolites" include terpenoid compounds produced in the roots of the *T. wilfordii* plant (or mimics of such secondary metabolite) which show immunosuppressive activity, such as 16-hydroxy-triptolide, triptolide, tripchlorolide, triptdiolide, triptonide, 17-hydroxytriptolide, celastrol, salaspermic acid, triptophenolide, wilforlide B, sesquiterpene alkaloids, isowilfordine sesquiterpene esters, sesquiterpene polyol esters, phenanthrene derivatives, tripterygone, salaspermic acid, other diterpene lactone epoxide compounds, and diterpene quinones.

"Terpene" or "terpenoid compounds" refers to compounds biosynthesized from multiple isoprene ($C_5H_8$) units originating from isopentenyl pyrophosphate, and whose backbone structures generally contain multiples of five carbon atoms. However, compounds with non-multiples of five carbons are also included, where one or more carbon atoms have been removed or added during bioprocessing.

"Sesquiterpene" refers to a terpene compound formed from 3 isoprene units; "diterpene" to a terpene compound formed from 4 isoprene units; and "triterpene" to a terpene compound formed from 6 isoprene units. Examples of sesquiterpenes produced in *Tripterygium wilfordii* (TW) include the sesquiterpene alkaloids reported by Ya (1990, 1991), and triptogelin and its derivatives (Takaishi, 1990, 1991a,b,c, 1992). Examples of diterpenes include 16-hydroxytriptolide (Ma, 1991a; 1992a), triptonide (Wu, 1992), triptriolide (Ma, 1991b), salaspermic acid (Chen, 1992), triptolide, tripchlorolide, tripdiolide, triptolidenol (Zheng, 1991), epitriptriolide (Ma, 1992b), and triptoquinones A and B (Shishido, 1993). Examples of triterpenes include tripterygic acid A (Zhang, 1990b), and tripterygone and its derivatives (Zhang, 1991).

"Alkyl" refers to a fully saturated monovalent radical containing only carbon and hydrogen, and which may be cyclic, branched or a straight chain. Examples of alkyl groups are methyl, ethyl, n-butyl, n-heptyl, isopropyl, 2-methylpropyl, cyclopropyl, cyclopropylmethyl, cyclobutyl, cyclopentyl, cyclopentylethyl, and cyclohexyl.

"Lower alkyl" refers to an alkyl radical of one to six carbon atoms, as exemplified by methyl, ethyl, n-butyl, i-butyl, t-butyl, isoamyl, n-pentyl, and isopentyl.

"Phenyl" refers to a substituted or unsubstituted monovalent benzene ring which may be substituted with one or more of the following: $NH_2$, $NHCH_3$, $OCH_3$, $OCF_3$, $CH_3$, and $CH_2CH_3$.

"Benzyl" refers to $CH_2Ph$, where the phenyl (Ph) group may be substituted as in the preceding paragraph.

II. Isolation of *Fusarium subglutinans f.sp. tripterygii*

The present invention is based on the discovery that *Fusarium subglutinans* fungal isolates associated as one of the endophytes of *T. wilfordii* (TW) produce commercially useful levels of terpenoid compounds having immunosuppressive activity. This section describes methods for obtaining such fungal organisms from the TW plant in accordance with the invention.

The TW plant may be readily obtained from Taiwan, the People's Republic of China, and various commercial sources in the United States. Growth conditions are preferably similar to those found in the native ranges for TW in mainland China, i.e., mildly acidic soil and subtropical climate conditions with direct sunlight.

To obtain the Fusarium fungus from the TW plant, the plant stems (typically 15–20 cm in length and about 1–3 cm in diameter) are collected and surface-treated with aqueous ethanol (70%) as a disinfectant. For a given stem, the outer back of the stem is removed using a sterile blade, followed by removal of small pieces of the inner back which are then transferred to an aqueous agar medium (e.g., 15 g agar/liter of water) in a Petri dish). Incubation of the stem material at 23° C. leads to hyphal growth of the endophytic fungi, typically within 3–5 days.

Following hyphal growth, tips of the fungal hyphae are removed, placed on plates of mycological agar (Difco Laboratories, Detroit, Mich.), and incubated at 23° C. Whether the culture is a *Fusarium subglutinans* species is determined according to morphological criteria defined above. A culture is judged to be pure if it presents an approximately circular growth with radial symmetry, in the absence of satellite colonies. Plugs of the pure fungi are then transferred to standard fungal culture medium and incubated under stationary conditions for 2–4 weeks. One culture medium suitable for growth of the Fusarium is M1D medium prepared as described in Pinkerton and Strobel (1976).

After incubation, the culture fluid is filtered through cheesecloth to remove fungi and clarify the culture fluid. Ethyl acetate is then added, and the combined fluids are mixed in a separatory funnel to extract the terpene compounds from the culture fluid. After the fluid layers have separated, the ethyl acetate layer is removed and taken to dryness under reduced pressure, typically affording 10–50 mg of dried residue per liter of culture medium. Details of the above procedure can be found in Example 1.

III. Production of Terpenoid Immunosuppressant Compounds

In one aspect, the present invention provides a method for producing a TW secondary metabolite compound (or a mimic of such a compound) having immunosuppressive activity, in greater amounts than available from extracts of the TW plant itself. In the method, Fusarium fungi obtainable from a stem of TW plant are grown in a culture medium as above, and then extracted with an organic solvent to collect TW secondary metabolites from the culture fluid. Suitable organic solvents for extraction include ethyl acetate, chloroform, and methylene chloride.

The dried extract resulting from the extraction procedure is further purified by chromatographic methods including silica gel chromatography and reverse-phase HPLC. In each purification step, fractions are collected and assayed for the presence of immunosuppressive activity using standard assays. Three assays which may be used for this purpose are given in Examples 5–7. Fractions found to contain activity are then subjected to further purification steps until the compound(s) giving rise to the observed activity have been purified to homogeneity.

Applying the foregoing approach, the applicants have identified several other fungal isolates within the Fusarium genus which also produce terpenoid products having immunosuppressive activity.

IV. Isolation and Characterization of Subglutinol

This section describes how the procedures above were used to obtain two novel immunosuppressive terpene compound, subglutinols A and B, in amounts suitable for commercial applications. The structures of these compounds are given in FIGS. 8A and 8B, respectively.

A. Isolation of Subglutinol from Fungal Culture

A protocol for isolating the subglutinol compounds from the Fusarium isolate of Example 1 is reported in Example 2. In brief, dried ethyl acetate extract obtained as described in Example 1 is loaded on a silica gel column equilibrated in a 95:5 (v:v) mixture of CH2C12: methanol and eluted by step gradient using 90:10 $CH_2Cl_2$: methanol. Aliquots of collected fractions are dried and tested for immunosuppressant activity using the assay in Example 6. Fractions showing activity in the assay are combined and may then be separated by reverse-phase C-18 HPLC using a water-methanol gradient.

Figure 2:
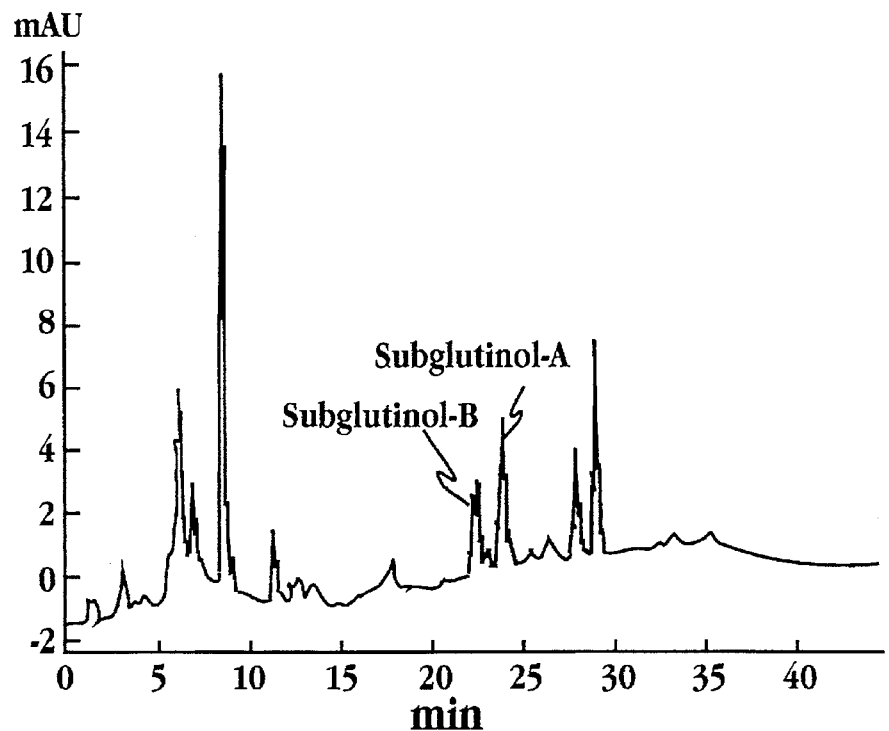

A chromatogram obtained in this HPLC step is shown in FIG. 2. As can be seen, the elution conditions are effective to baseline-resolve subglutinols A and B from one another, with elution times of about 22.5 and 24 minutes, respectively. Re-chromatography of the isolated subglutinols on the C-18 column can be used to eliminate contaminants eluting as shoulders adjacent the subglutinol peaks. Using the protocols in Examples 1 and 2, subglutinol yields as high as 6.5 mg/L of culture medium were obtained.

B. Structure Analysis

Figure 8A:
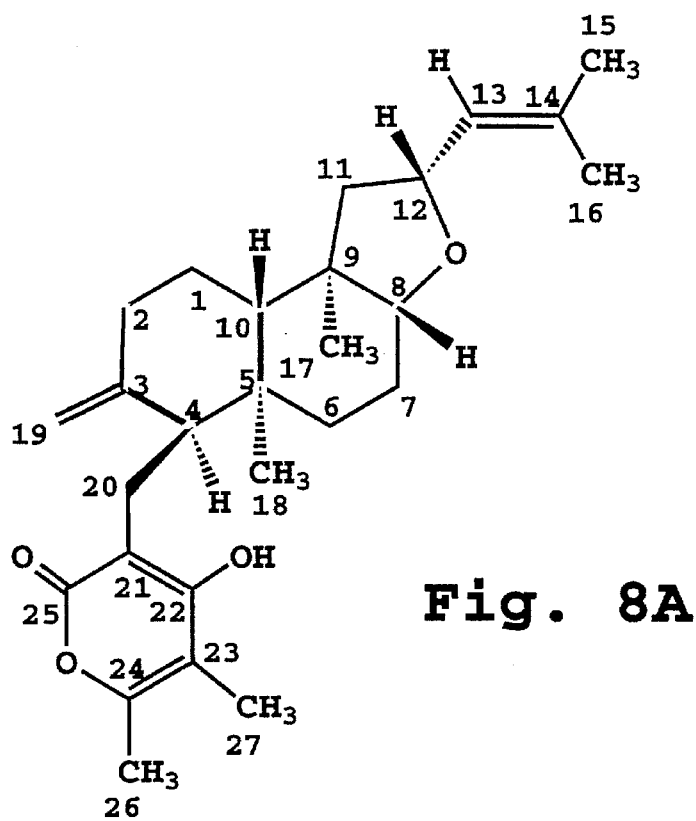
Figure 8B:
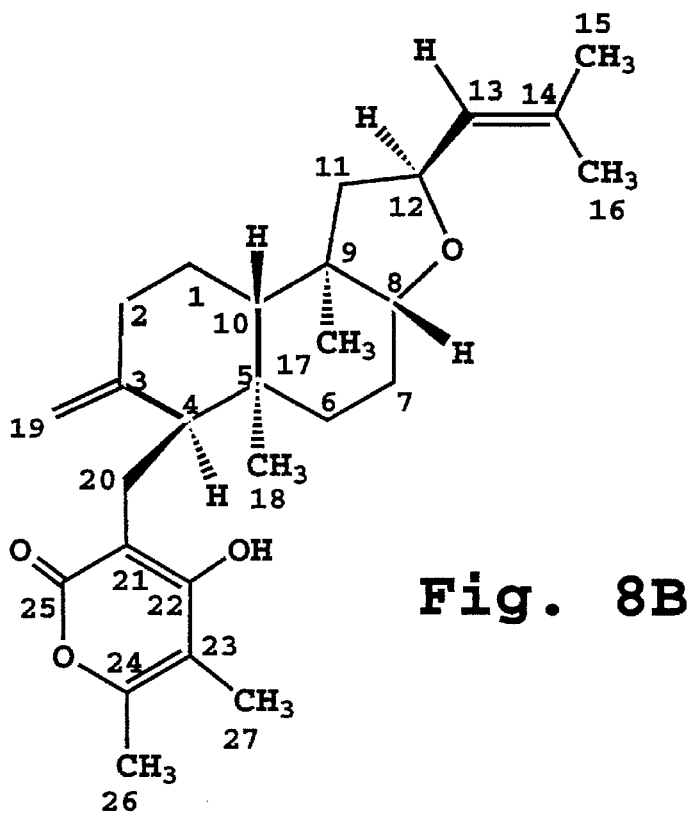

The subglutinol compounds isolated as described above were characterized by a number of physicochemical techniques, leading to determination of the structures shown in FIGS. 8A and 8B. It is noted that the absolute stereochemistry of these compounds was not determined. Accordingly, the present invention contemplates the structures shown in FIGS. 8A and 8B.

Figure 3:
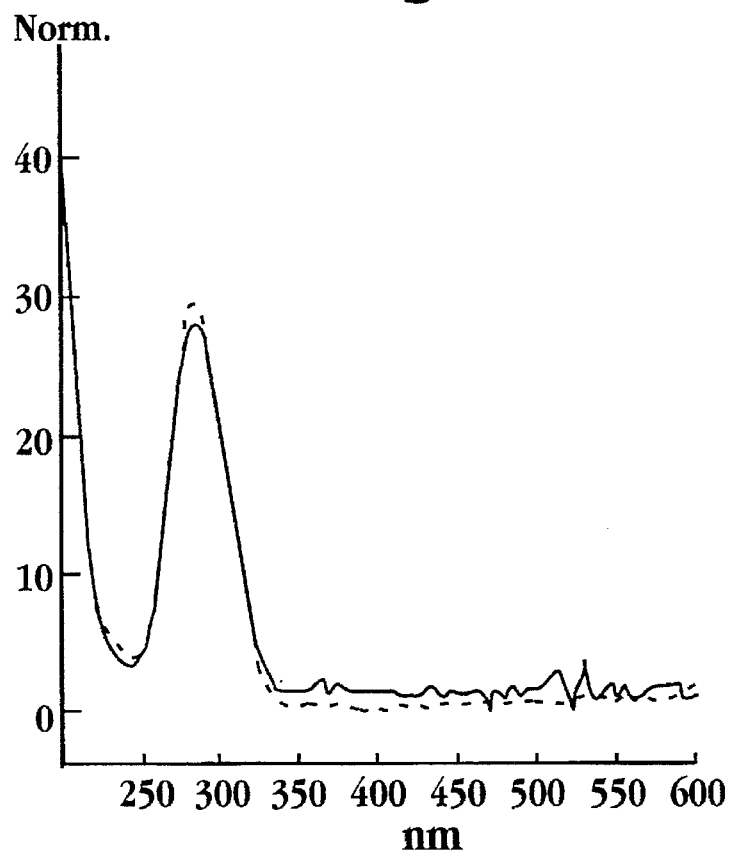
Figure 4:
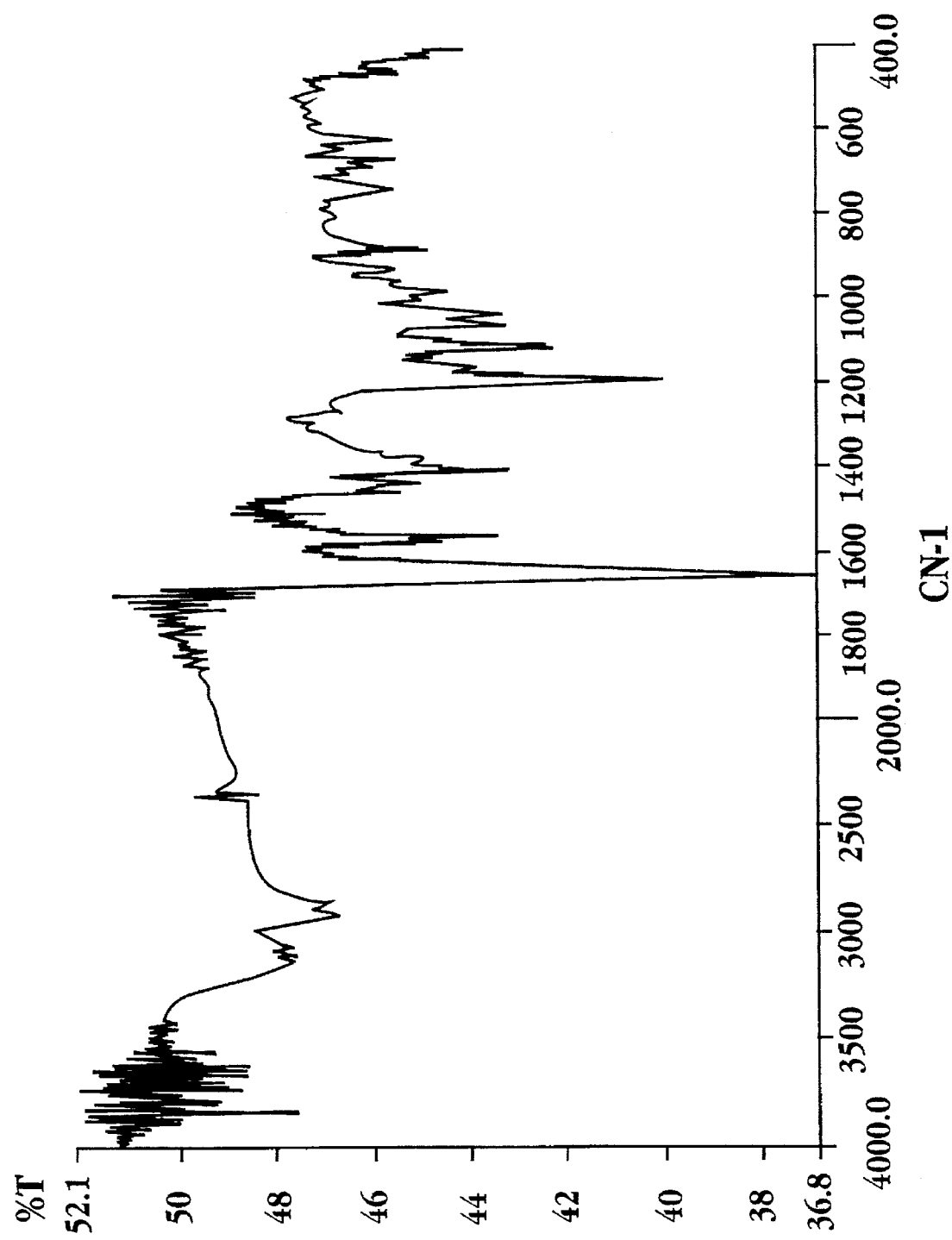
Figure 5:
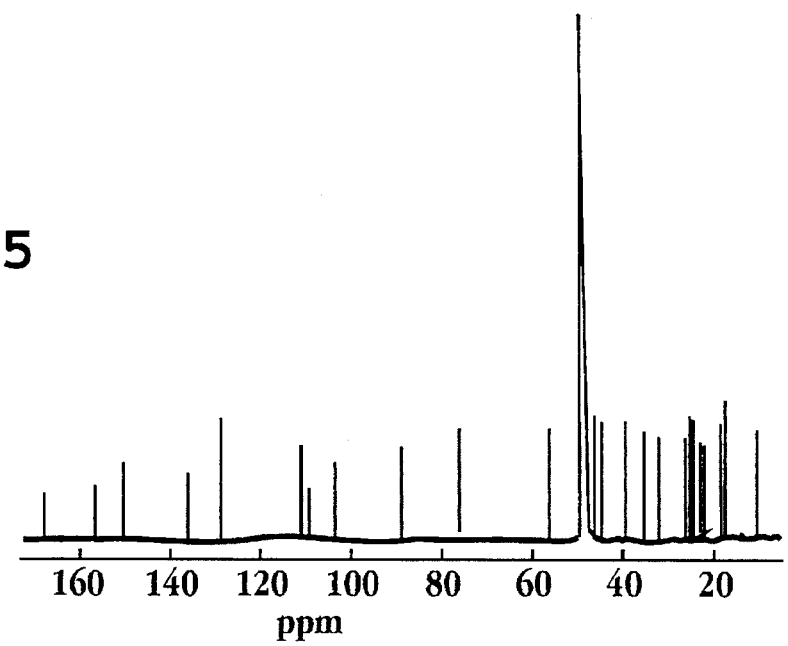
Figure 6A:
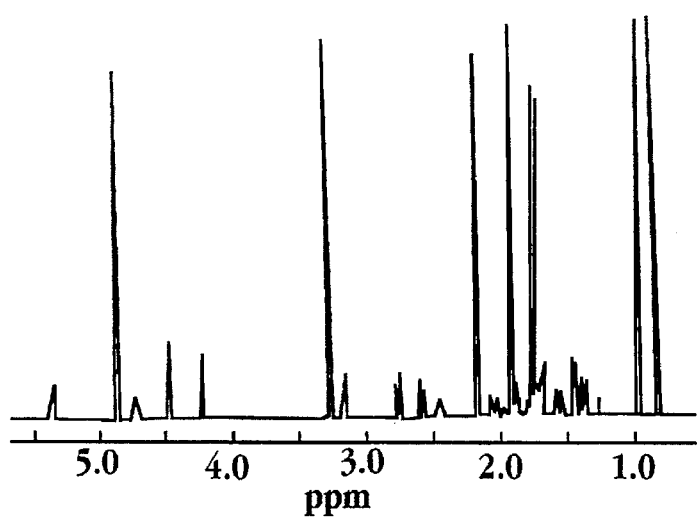
Figure 6B:
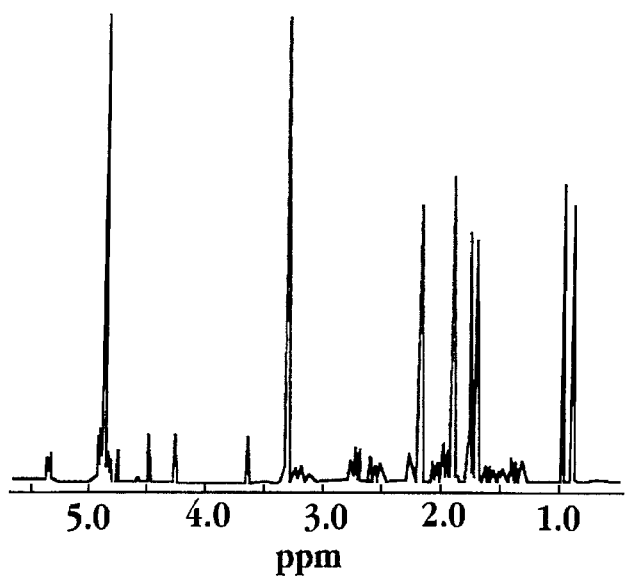

Considering the physical properties of these compounds, subglutinols A and B showed substantially the same UV-absorption properties in the range of 200–600 nm, with maximum absorbance at 294 nm (FIG. 3). The infrared spectrum of subglutinol A showed a strong absorbance peak at 1661 cm$^{-1}$ (FIG. 4), consistent with a β-hydroxy α, β, γ, δ-unsaturated δ-lactone ring.

Figure 7A:
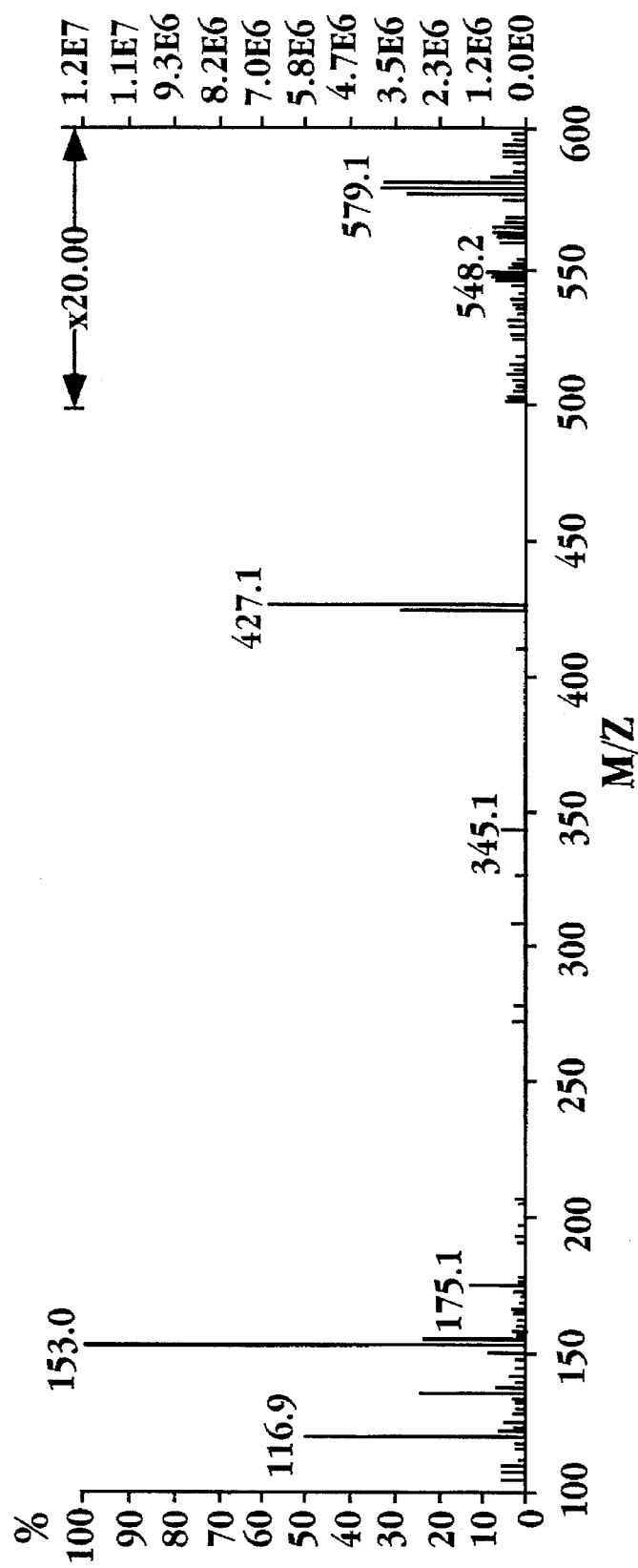
Figure 7B:
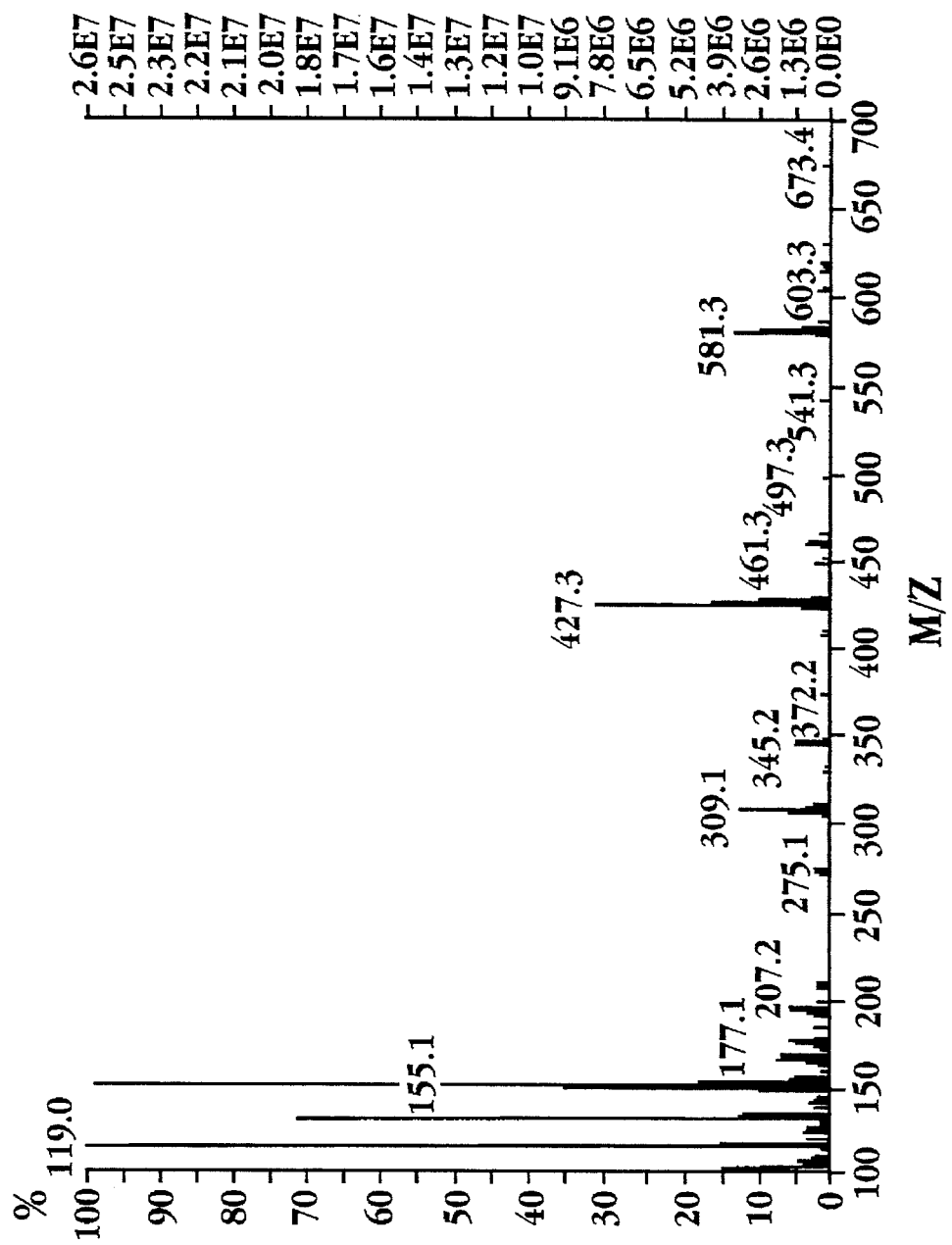

Fast atom bombardment mass spectrometry (FABS) of subglutinols A and B separately revealed in each case a molecular mass of 426.3 (FIGS. 7A and 7B). The molecular formula was determined to be $C_{27}H_{38}O_4$ based on high resolution mass spectrometric measurements for both subglutinols A and B.

One- and two-dimensional NMR data collected for the two compounds are summarized in Tables 1 and 2. Column 1 in each table lists the carbon numbers (1 to 27) of the subglutinol compounds in accordance with the numbering shown in FIGS. 8A and 8B. This numbering also applies to the hydrogen atoms attached to each carbon. Columns 2 and 3 in each table list the one-dimensional shifts from the $^{13}C$ and $^{1}H$ spectra, respectively. Column 4 (HMBC) lists proton cross-peaks with respect to the $^{13}C$ shifts in column 2, and column 5 (ROESY) lists proton cross-peaks with respect to the proton shifts shown in column 3.

All of the NMR spectra were obtained in deuterium-exchanged methanol (MeOD). Resonance peaks were detected for all 27 carbons and 38 hydrogens, with peak assignments established by 2-dimensional NMR techniques (HMQC, HMBC and ROESY). Taken together, the data support the structures shown in FIGS. 8A and 8B.

TABLE 1

NMR Data for Subglutinol A

| Carbon # | 13-C[1] | 1-H[2] | HMBC[3] | ROESY[4] |
|---|---|---|---|---|
| 1 | 26.2 (t) | 1.56 (qd, 13.3, 4.9) | 2.45 | |
| | | 1.45 | | |
| 2 | 32.1 (t) | 2.45 (td, 13.1, 5.6) | 4.50, 4.25, 2.17, 1.56 | 1.74, 2.05, 1.45 |
| | | 2.05 (br dd, 13.2, 4.6) | | |
| 3 | 149.9 (s) | | 2.74, 2.58, 2.45, 2.17, 2.05 | |
| 4 | 56.5 (d) | 2.17 (dd, 11.3, 4.5) | 4.50, 4.25, 2.05, 0.96 | 2.74, 2.58, 0.96 |
| 5 | 39.6 (s) | | 2.17, 0.96 | |
| 6 | 35.9 (t) | 1.90 | 1.78, 0.96 | |
| | | 1.38 (dt, 13.7, 3.3) | | |
| 7 | 23.3 (t) | 1.78 | | |
| | | 1.74 | | 0.96, 0.85 |
| 8 | 88.6 (d) | 3.17 (dd, 11.4, 3.8) | 1.45, 0.85 | 1.90, 1.78, 1.69, 1.38 |
| 9 | 45.5 (s) | | 1.45, 0.86 | |
| 10 | 46.5 (d) | 1.74 | 2.17, 2.05, 1.90, 0.96, 0.85 | |
| 11 | 49.0 (t) | 1.90 | 3.17, 0.85 | |
| | | 1.45 (dd, 11.7, 3.5) | | 0.85 |
| 12 | 75.9 (d) | 4.75 (td, 9.1, 3.6) | 1.90 | 3.17, 1.90, 1.69, 1.45 |
| 13 | 128.4 (d) | 5.35 (br dt, 8.6, 1.3) | 1.90, 1.72, 1.69, 1.45 | 1.72, 1.45, 0.85 |
| 14 | 136.4 (s) | | 1.72, 1.69 | |
| 15 | 25.8 (q) | 1.72 (d, 0.8) | 5.35, 1.69 | |
| 16 | 18.2 (q) | 1.69 (d, 1.2) | 5.35, 1.72 | |
| 17 | 17.5 (q) | 0.85 s | 3.17, 1.90, 1.45 | 1.74, 1.45 |
| 18 | 25.1 (q) | 0.96 s | 2.17, 1.90, 1.74 | 1.74 |
| 19 | 110.7 (t) | 4.50 (t, 2.4) | | |
| | | 4.25 (t, 2.4) | 2.45, 2.05, 2.17 | 2.17, 0.96 |
| 20 | 22.7 (t) | 2.74 (dd, 13.1, 11.4) | | 1.74 |
| | | 2.58 (dd, 13.1, 4.4) | | 1.90, 1.74 |
| 21 | 103.7 (s) | | 2.74, 2.58 | |
| 22 | 165.30 (s) | | 2.74, 2.58, 1.91 | |
| 23 | 109.0 (s) | | 2.19, 1.91 | |
| 24 | 156.8 (s) | | 2.19, 1.91 | |
| 25 | 165.35 (s) | | 2.74, 2.58 (1.91?) | |
| 26 | 17.3 (q) | | | |
| 27 | 10.4 (q) | | | |

1$^{13}$C shifts in ppm, multiplicity in parentheses.
2$^{1}$H shifts in ppm, multiplicity and coupling constants (Hz) in parentheses; assignments by HMQC.
3$^{13}$C-$^{1}$H proton correlation peaks.
4$^{1}$H-$^{1}$H proton correlation peaks.

TABLE 2

NMR Data for Subglutinol B

| Carbon # | 13-C[1] | 1-H[2] | HMBC[3] | ROESY[4] |
|---|---|---|---|---|
| 1 | 26.2 (t) | 1.57 (qd, 12.9, 4.6) | | |
|   |          | 1.44 | | |
| 2 | 32.1 (t) | 2.48 (bd, 13.2, 4.9) | 4.50, 4.25 | |
|   |          | 2.05 (br d) | | 1.76 |
| 3 | 150.0 (s) | | 2.56, 2.48, 2.23 | |
| 4 | 56.4 (d) | 2.23 (dd, 11.2, 4.6) | 4.50, 4.25, 2.74, 2.56, 0.96 | 4.25, 0.96 |
| 5 | 39.5 (s) | | 2.23, 0.96 | |
| 6 | 35.9 (t) | 1.91 | | 2.56, 1.37 |
|   |          | 1.37 (dt, 13.5, 2.9) | | 1.91, 0.96 |
| 7 | 23.5 (t) | 1.90 | | |
|   |          | 1.67 (dd, 7.3, 3.5) | | |
| 8 | 87.4 (d) | 3.31 | 1.90, 0.87 | 5.35, 1.91, 1.76, 1.30 |
| 9 | 46.0 (s) | | | |
| 10 | 46.1 (d) | 1.76 (dd, 9.3, 3.7) | 2.23, 1.97, 1.30, 0.96 | 2.74, 2.05 |
| 11 | 49.4 (t) | 1.97 (dd, 11.2, 6.8) | 4.84, 0.87 | |
|    |          | 1.30 (dd, 11.2, 9.2) | | 5.35, 3.31, 1.97 |
| 12 | 75.5 (d) | 4.84 | | 1.97, 1.68, 0.87 |
| 13 | 128.0 (d) | 5.35 (dt, 8.3, 1.0) | 1.74, 1.68, 1.30 | 3.31, 1.74, 1.30 |
| 14 | 135.5 (s) | | 1.74, 1.68 | |
| 15 | 24.9 (q) | 1.74 (d, 1.0) | 5.35, 1.68 | 5.35 |
| 16 | 18.0 (q) | 1.68 (d, 0.9) | 5.35, 1.74 | 4.84 |
| 17 | 16.1 (q) | 0.87 (s) | 1.30 | 4.84, 1.97 |
| 18 | 25.1 (q) | 0.96 (s) | | 2.23, 1.37 |
| 19 | 110.5 (t) | 4.50 (t, 1.7) | 2.23 | 2.05 |
|    |           | 4.25 (t, 1.7) | | 2.23, 0.96 |
| 20 | 22.8 (t) | 2.74 (dd, 12.8, 11.2) | | 1.76 |
|    |          | 2.56 (dd, 12.8, 4.64) | | 1.91 |
| 21 | 102.9 (s) | | 2.74, 2.56 | |
| 22 | 168.6 (s) | | 2.74, 2.56, 1.90 | |
| 23 | 110.4 (s) | | 2.17, 1.90 | |
| 24 | 156.3 (s) | | 2.17, 1.90 | |
| 25 | 168.6 (s) | | 2.74, 2.56 | |
| 26 | 17.3 (q) | 2.17 (s) | | |
| 27 | 10.5 (q) | 1.90 (s) | | |

[1] $^{13}$C shifts in ppm, multiplicity in parentheses.
[2] $^{1}$H shifts in ppm, multiplicity and coupling constants (Hz) in parentheses; assignments by HMQC.
[3] $^{13}$C-$^{1}$H proton correlation peaks.
[4] $^{1}$H-$^{1}$H proton correlation peaks.

C. Subglutinol Analogs

In a related embodiment, the invention includes novel immunosuppressant compounds having structures in accordance with formula II above, as illustrated in FIGS. 9A–9E.

Figure 9A:
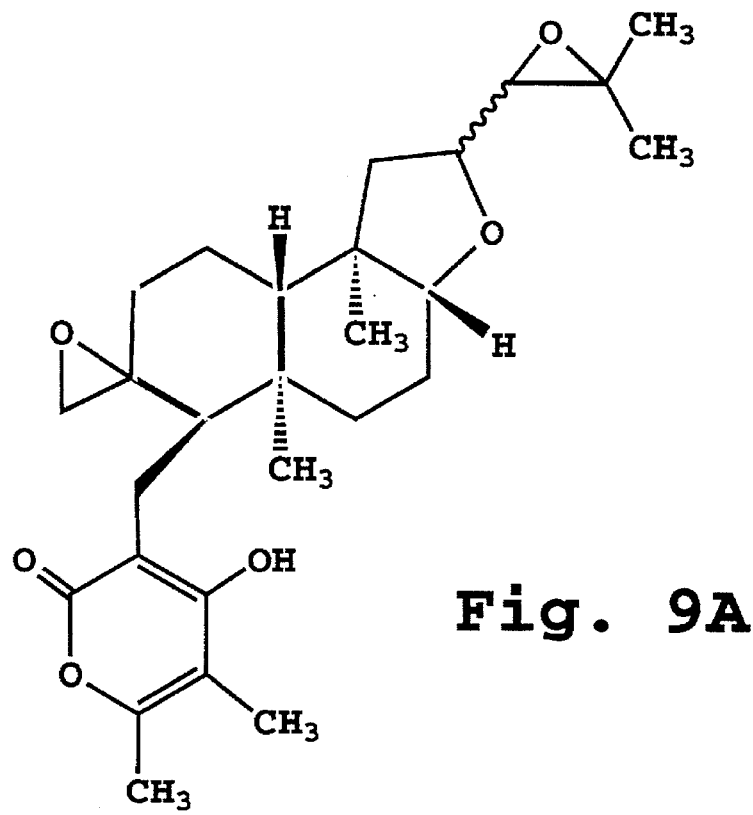

The diepoxide analog of FIG. 9A may be prepared by epoxidation of subglutinol by standard methods, e.g., by reaction of subglutinol with m-chloroperbenzoic acid as described in Paquette and Barrett (1967, 1973). The reaction conditions are chosen to promote epoxidation of the non-conjugated olefins at C-3 and C-13 to the exclusion of the conjugated double bonds present in the pendent lactone ring.

The diepoxide product may be used to bind covalently to biological targets by virtue of covalent reaction of nucleophilic groups in the target with the epoxide moieties. In addition, the diepoxide may be used to prepare the tetrahydroxy analog shown in FIG. 9B by standard methods, e.g., by acid-catalyzed hydrolysis of the epoxide groups as described by Swern (1946).

Figure 9B:
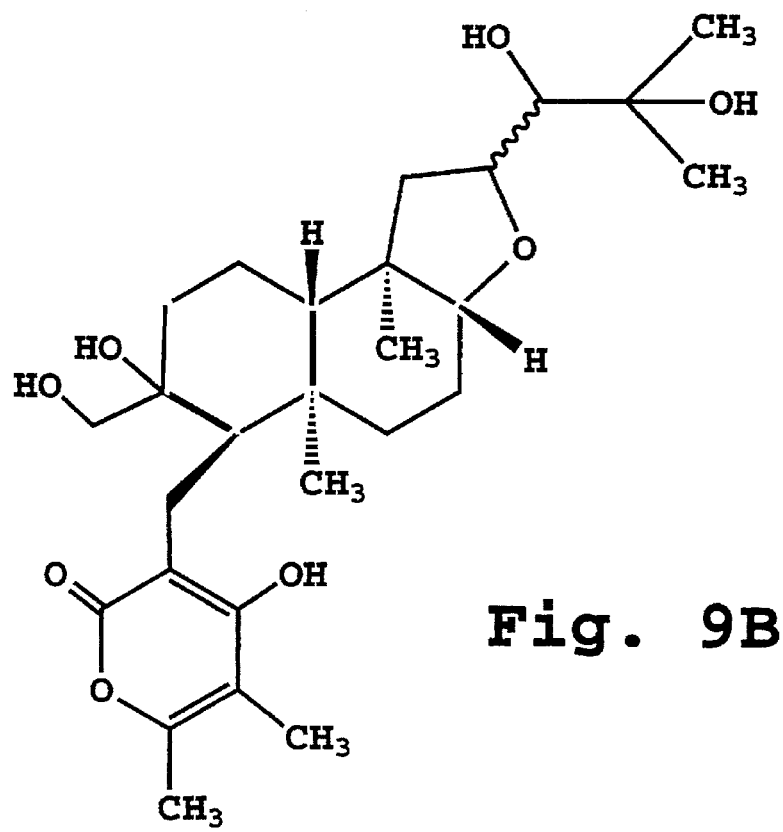

In an alternative approach, the FIG. 9B analog can be prepared by oxidation of subglutinol with potassium permanganate under basic conditions (e.g., Wiberg, et al., 1960, 1966; or by reaction with osmium tetroxide followed by mild reduction, e.g., Gunstone (1960); Rocek and Westheimer (1980, 1962).

Figure 9C:
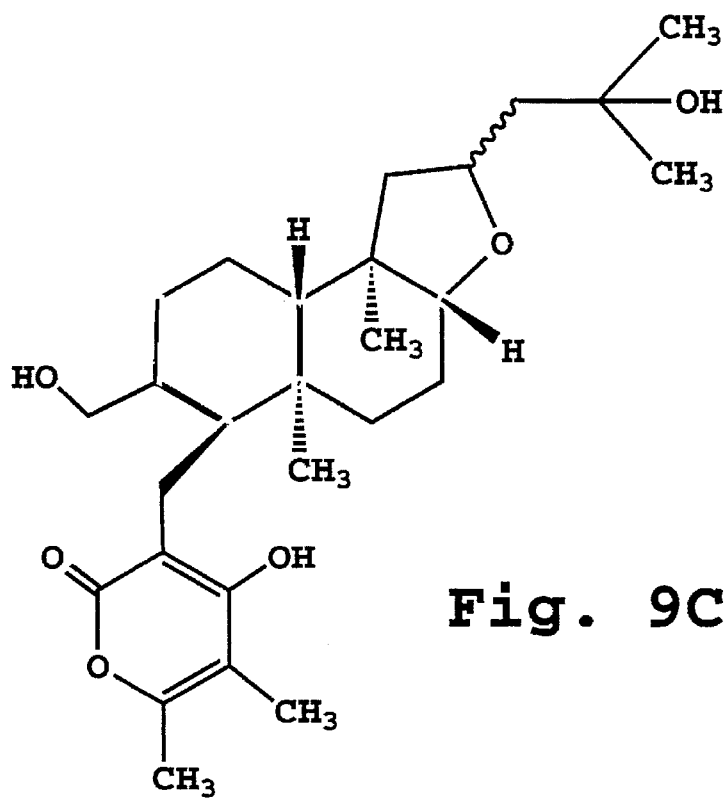

The subglutinol triol analog shown in FIG. 9C can be prepared by hydroboration followed by oxidation with hydrogen peroxide as described, for example, in J. Am. Chem. Soc. 88:5851 (1966) and J. Org. Chem. 51:4925 (1986). These conditions effect the net addition of $H_2O$ across the affected alkene groups such that the added hydroxyl groups reside on the less sterically hindered carbon atoms.

Figure 9D:
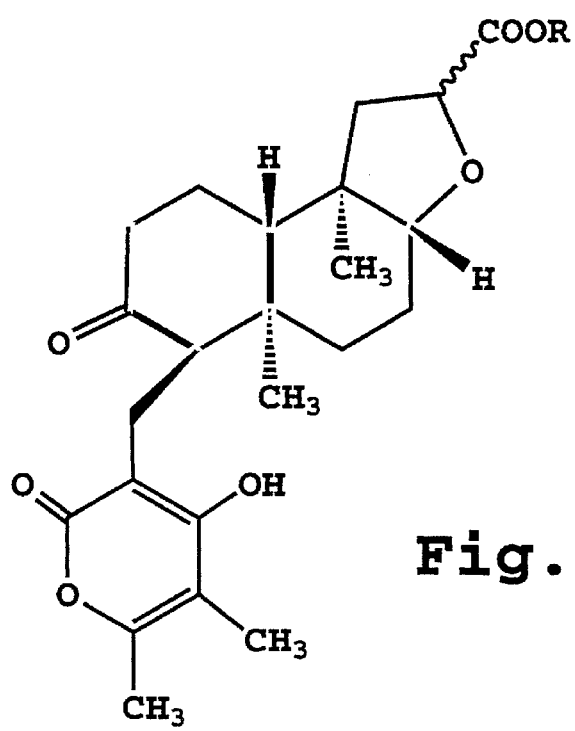
Figure 9E:
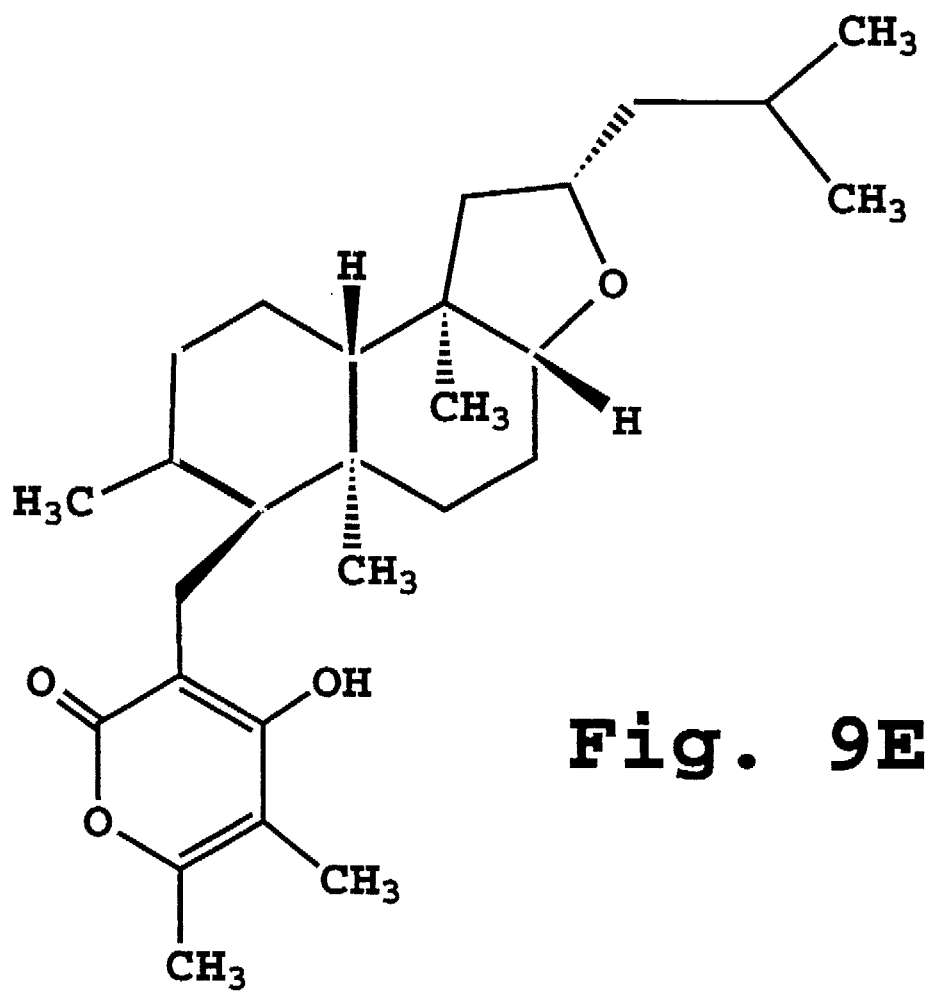

The C-3-keto/C-13-ester analog shown in FIG. 9D can be prepared by oxidative cleavage of the alkene groups at C-3 and C-13, e.g., by ozonolysis to produce the 3-keto-13-aldehyde analog of subglutinol, followed by oxidation in the presence of the desired alcohol (ROH, where R is as defined for Formula II) to produce the 3-keto-13-ester product shown in FIG. 9D. Alternatively, the product in FIG. 9D may be obtained by oxidative cleavage of the bis-cis-diol from FIG. 9B with periodate or permanganate in the presence of ROH.

Subglutinol can also be modified to form a more saturated analog (FIG. 9E) by mild reduction of the alkene groups at C-3 and C-13 using hydroboration/ protonolysis (J. Am. Chem. Soc. 81:4108 (1959)), hydrogenation with diimide or tosyldiimide (J. Org. Chem. 30:3965 (1965); J. Org. Chem. 52:4665 (1987); or catalytic hydrogenation using Raney nickel or palladium over carbon in the presence of hydrogen gas.

D. Biological Properties

Purified subglutinol (a mixture of subglutinol A and subglutinol B) was examined for immunosuppressive activity in a variety of biological assays.

One measure of immunosuppression is suppression of stimulated proliferation of peripheral blood lymphocytes (PBLs) in vitro. In the assay detailed in Example 5, PBLs were activated in vitro by addition of anti-CD3 monoclonal antibody (X-35 antibody). Subglutinol or vehicle (control) was added to each culture, at selected concentrations. After 72 hours incubation, tritiated thymidine was added to the culture medium, and incorporation of tritium into DNA was assayed as a measure of DNA synthesis associated with cell proliferation.

Figure 10:
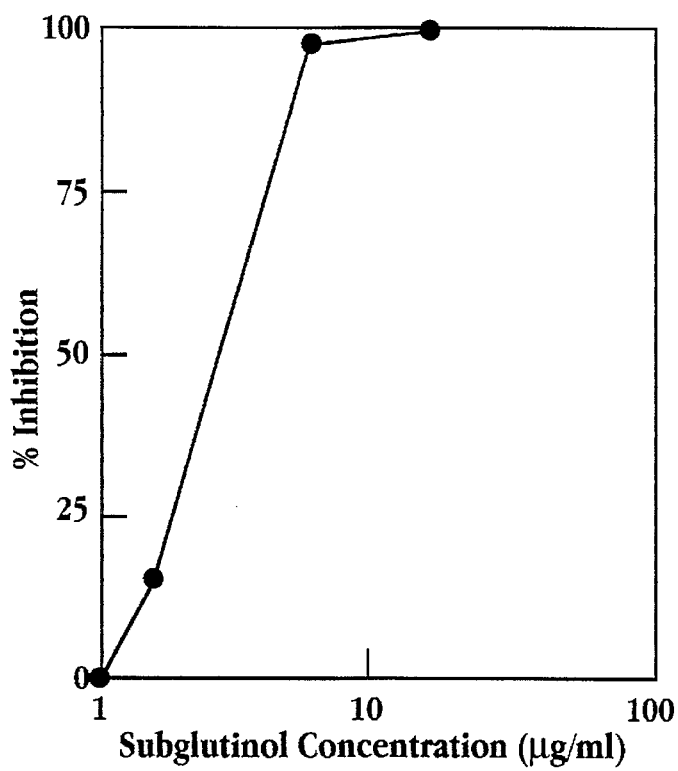

FIG. 10 shows inhibition of peripheral blood lymphocyte proliferation as a function of subglutinol concentration. As seen, increasing amounts of subglutinol produced dose-dependent suppression of proliferation of anti-CD3 stimulated PBLs.

Figure 11:
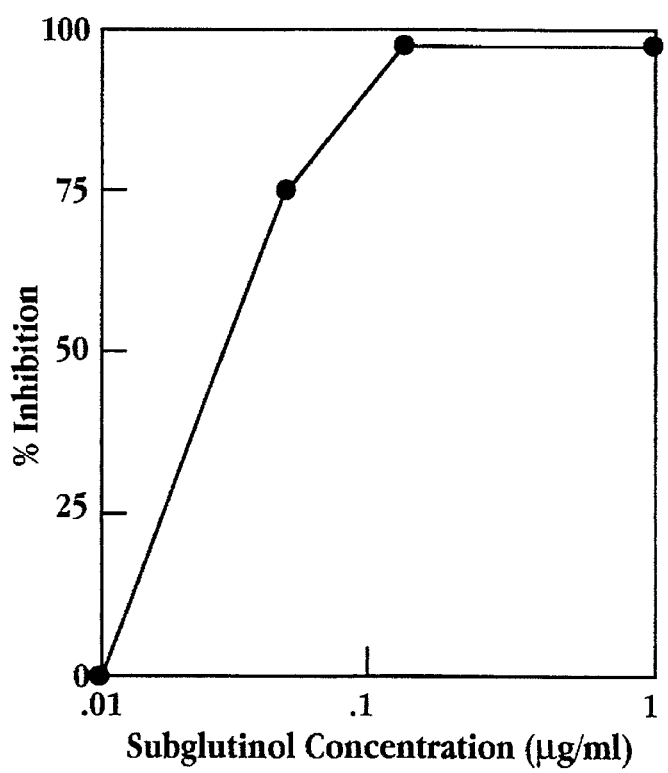

The ability of subglutinol to suppress the cell-proliferative effect of IL-1 in mouse thymocytes as an index of IL-1 action (O'Gara, 1990) was also examined. In this study, mouse thymocytes in culture were stimulated with IL-1 in the presence of phytohemagglutinin and increasing concentrations of subglutinol. The cells were cultured for 72 hours, and during the last four hours, incubated with tritiated thymidine. FIG. 11 shows the inhibition of cell proliferation in cells over the concentration range of 0.012 to 0.76 µg/ml culture medium. Nearly complete inhibition of IL-1 action on thymocytes was observed at about 0.2 µg/ml subglutinol. Details are given in Example 6.

A measure of immunosuppression that serves as a model for transplantation rejection is inhibition of cell proliferation in a mixed lymphocyte reaction (MLR) assay (Bradley, in Mishell, 1980). In these experiments, an MLR is induced by co-incubating responder (R) cells from one mouse strain (C57B1/6) with stimulator (S) cells from another mouse strain (Balb/C).

The responder cells proliferate in the presence of the allogenic stimulator cells. The stimulator cells are irradiated so they are unable to proliferate. After 72 hours incubation, tritiated thymidine is added to the mixed cell cultures, and incorporation of the labeled nucleotide into DNA is assayed as an index of cell proliferation.

Figure 12:
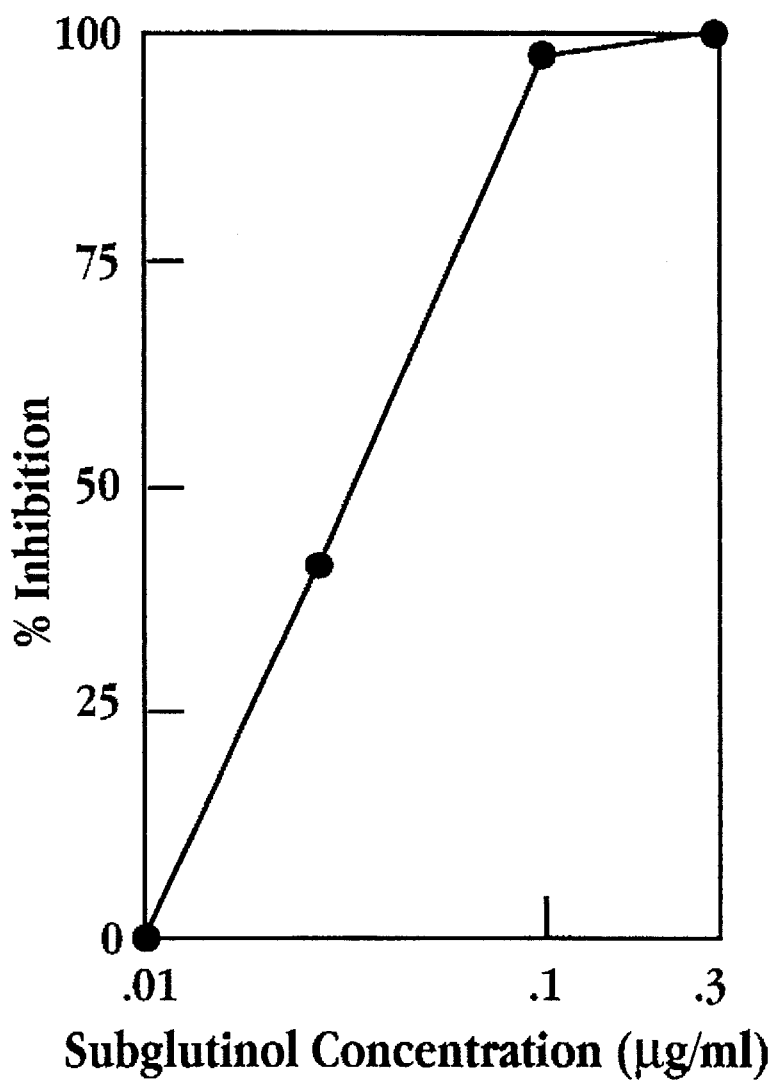

In the MLR test reported in Example 7, responder cells were co-cultured in microtitre wells with stimulator cells, in the presence of selected concentrations of subglutinol between 0.01 and 0.3 µg/ml. The wells receiving no subglutinol would be expected to be maximally stimulated. The cells were cultured for 4 days, and labeled with [$^3$H] thymidine during the last 18 hours of incubation. Percent inhibition of stimulation is shown in FIG. 12. Nearly complete inhibition was observed at 0.1 µg/ml.

Potential toxicity of the mixture was assessed by measurement the effect of subglutinol on the ability of cultured cells to reduce MTT (3-[4,5-Dimethylthiazol-2-yl]-2,5-diphenyltetrazolium bromide), an index of cellular respiration that is more sensitive in the detection of cytotoxicity than methods involving measurement of DNA replication (Green, 1984).

E. Presence of Subglutinols in TW Plant

The relative advantages of obtaining TW secondary metabolites from cultured Fusarium fungi instead of from the TW plant itself can be appreciated from the study described in Example 4. To determine whether subglutinol could be detected in TW plant extract, the TW root xylem was subjected to ethanol extraction to collect organic-soluble components, followed by extraction of the ethanolic extract with methylene chloride. The methylene chloride fraction was then chromatographed by 2-dimensional TLC to separate any subglutinol in the mixture from other components. Two rounds of preparative TLC afforded material which comigrated with authentic subglutinol, and which showed the same molecular weight, thereby confirming that the material from the TW plant was subglutinol.

The amount of subglutinol in the plant extract was estimated to be less than 0.1% of the total organic solvent extract, in contrast to the proportion of roughly 0.2% of total fungal cell mass when isolated from cultured Fusarium.

III. Utility

The subglutinol compound of the invention and analogs thereof (FIGS. 8 and 9) are useful in treating a variety of autoimmune conditions, such as rheumatoid arthritis, allergies, asthma, lupus erythematosus, and psoriasis.

In a general treatment method, subglutinol, alone or in combination with another type of immunosuppressants, such as cyclosporin A, FK506, azathioprine, methotrexate, rapamycin, mycophenolic acid, and/or a glucocorticoid, is administered in a therapeutically effective amount, i.e., an amount effective to reduce the clinical symptoms of the autoimmune disease.

The compound may be administered by oral or parenteral administration, such as IV administration. For oral administration, the compound may be given in tablet or capsule form, at a preferred dose of 0.1 and 2 mg/kg patient body weight per day. The dose may be increased or decreased appropriately depending on the response of the patient and patient tolerance.

A parenteral suspension can be administered by injection, e.g., intravenously, intramuscularly, or subcutaneously. A dose between about 0.05 and 1 mg subglutinol/body weight per day is preferred, and this level may be increased or decreased appropriately, depending on the conditions of disease, the age of the patient, and the ability of the patient to resist infection.

The compound may also be used in the treatment of transplantation rejection of cardiac, kidney, liver, and bone marrow transplants, and cellular transplants, by administering to the patient subglutinol alone or in combination with cyclosporin A, FK506, azathioprine, methotrexate, rapamycin, mycophenolic acid, and/or a glucocorticoid. Initial treatment is administered perioperatively. In addition, the compound may be administered chronically to prevent graft rejection. Finally, the compound may also be used to treat episodes of late graft rejection.

From the foregoing, it can be seen how various objects and features of the invention are met. The invention provides a method for producing terpenoid compounds that are normally produced as secondary metabolites in *T. wilfordii*, at greater levels than obtainable from the root tissues of *T. wilfordii* alone. The approach allows production of these compounds on a commercial scale, as immunosuppressive and anti-inflammatory agents, heretofore impractical because of the difficulty and cost of obtaining such quantities from TW plants.

The method can also lead to the production and identification of new secondary metabolites present in *T. wilfordii* extracts, such as the subglutinol compound described herein.

The following examples illustrate methods for obtaining purified extract, and demonstrate various physical, chemical, and biological properties of the extract. The examples are intended to illustrate, but in no way limit the scope of the invention.

EXAMPLE 1

Isolation of Fusarium Fungus

Stems (15–20 cm length×1–3 cm diameter) of *T. wilfordii* were collected from its native range in China. After each stem fragment was surface-treated with 70% ethanol as disinfectant, the outer bark was removed using a sterile blade. Small pieces of the inner bark were then removed by sterile blade as well and placed on a Petri plate containing water agar (15 g agar/liter $H_2O$). Hyphal growth of the endophytic fungi occurs within 3–5 days.

Tips of the fungal hyphae were removed from the water agar and subsequently placed on mycological agar (Difco). The culture was judged pure based on its behavior on the plate. Lab or bark contaminants rarely occurred, due to the use of aseptic methods.

Once obtained in pure form, fungi (2 or 3 0.5–1 $cm^2$ plugs per flask) were transferred to two 2-liter flasks, each containing 500 mL M1D liquid medium (Pinkerton, 1976), and the flasks were incubated at 23° C. under still conditions for 18–20 days. At the end of the incubation period, the culture fluid, along with the mycelium, was passed through 4 layers of cheesecloth.

To the clear, filtered fluid was added an equal volume of ethyl acetate, and the combined fluids were shaken in a separating funnel. After standing for 15–30 minutes, the ethyl acetate (upper layer) was removed and taken to dryness by flash evaporation at 35° C. under reduced pressure.

An electron micrograph of the fungal organism isolated from *T. wilfordii* is shown in FIG. 1. The organism was identified as a *Fusarium subglutinans* isolate species on the basis of the following features. The fungus has an extensive mycelium in culture with a cottony appearance. The older part of the culture has a pinkish coloration. The hyphae possess simple conidiophores, each producing a single oval conidium (microconidium), which commonly is engulfed in a droplet of water. The cultures, on occasion, also produce multiple hyaline-canoe-shaped septate macroconidia, which is characteristic of the Fusarium genus. No evidence of a sporodochium was observed. The isolated organism characterized above has been deposited with the American Type Culture Collection, Rocklawn MD under accession number ATCC 74358.

EXAMPLE 2

Purification and Chemical Characterization of Subglutinol

A. Isolation

Dried ethyl acetate extract (10–50 mg) from Example 1 was dissolved in a small amount of 95:5 $CH_2Cl_2$:MeOH (v/v) and applied to a silica gel column (5–10 cm×1 cm diameter, 40 micrometer mesh size, flash chromatography packing from Baker) equilibrated in the same 95:5 solvent mixture after the gel bed had been washed first with an equal volume of methylene chloride.

The column was eluted with 90:10 $CHC_2Cl_2$:methanol (v/v) and fractions were collected. The fractions with greatest ability to inhibit IL-1-stimulated thymocyte proliferation (Example 6) were combined and subjected to a final purification step by HPLC on a C18 semi-preparative column (25.0 cm×10.0 mm) with a MeOH/$H_2O$ solvent system. An initial 10 minute isocratic elution at 75% MeOH, followed by a linear gradient from 75% to 100% MeOH was effective to resolve and purify the two stereoisomers of subglutinol, subglutinol A and B. The solvent flow rate was 3.0 ml/min, with UV detection at 254 nm (see FIG. 2). The purified compounds were analyzed as described below. Using the procedure, yields of subglutinol (A+B) as high as 6.5 mg/L culture medium have been obtained. The two stereoisomers were isolated in a 4:1 ratio (A:B), as determined by $^1$H-NMR analysis (see below).

B. Chemical Analysis

UV spectra were obtained using a Hewlett Packard diode array spectrophotometer. The UV spectra obtained for subglutinols A and B are shown in FIG. 3.

Infrared spectra were obtained using a Perkin Elmer 1620 FT-IR spectrometer. An IR spectrum obtained for a mixture of subglutinols A and B is shown in FIG. 4.

$^1$H and $^{13}$C NMR spectra were obtained at 500 MHz and 100 MHz, respectively. Samples were dissolved in spectral grade MeOH. All shift values are given in ppm. The $^{13}$C spectrum obtained for a mixture of subglutinol A is shown in FIG. 5. Separate $^1$H NMR spectra for subglutinols A and B are shown in FIGS. 6A and 6B, respectively. In addition, several two-dimensional pulse sequences were used to provide connectivity information—homonuclear multiple quantum coherence spectroscopy (HMQC), proton detected long range heteronuclear multiple quantum spectroscopy (HMBC), and rotating frame Overhauser enhancement spectroscopy (ROESY). The NMR data are summarized in Tables 1 and 2 above.

Mass spectra were obtained using FAB mass spectrometry. Mass spectra obtained for subglutinols A and B are shown in FIGS. 7A and 7B, respectively. The determined mass for subglutinol A ($M+H^+$) was 427 daltons, giving a true molecular mass of 426 daltons (FIG. 7A). An identical mass determination was made for subglutinol B (FIG. 7B).

The molecular formula for subglutinols A and B were determined by high resolution mass spectrometry, based on the best fit of possible chemical formulas with the molecular mass observed.

Selected measured properties of subglutinols A and B are summarized below:

| | |
|---|---|
| Subglutinol-A | |
| Compound form | White powder |
| Molecular weight | 426.28 |
| Molecular formula | $C_{27}H_{38}O_4$ |
| UV $\lambda_{max}$/ext. coeff | 294 nm/8500 mAu/M · cm (MeOH) |
| IR (C = O) | 1661 $cm^{-1}$ |
| Melting Point | 185° C. |
| Subglutinol-B | |
| Compound form | White powder |
| Molecular weight | 426.30 |
| Molecular formula | $C_{27}H_{38}O_4$ |
| UV $\lambda_{max}$ | 294 nm (MeOH) |

EXAMPLE 3

Production of $^{14}$C Subglutinol from *Fusarium spp*

100 μCi $Na^{14}C$-1-acetate (47 mCi/mmol) was added to a 14 day old culture of *Fusarium spp* (Example 1). After incubating for 3 days at 23° C., the culture fluid was harvested, and subglutinol was purified according to the procedures in Example 2. The radioactivity recovered in subglutinol was $1.3\times10^{-5}$ dpm/mg ($5.4\times10^7$ dpm/mmol) from 2.4 g dry weight of mycelium. The total amount recovered was 1.2 mg.

The chromatographic purity of the $^{14}$C-labeled subglutinol was determined by 2 dimensional thin layer chromatography (2-D TLC) using authentic subglutinol as a control and carrier. The radiolabeled sample was placed on the origin along with the authentic subglutinol. After 2-D TLC using 95:5 ethyl acetate: isopropanol (v/v) in the first dimension, followed by 3:1 methylene chloride:tetrahydrofuran (v/v) in the second dimension, the plate was overlaid with an X-ray film for 1 week. Spraying the TLC plate with 1% vanillin sulfuric acid revealed a single spot.

Subsequently, overlaying the developed X-ray film on the plate revealed that the size, shape and location of the spots (X-ray film and TLC plate) were identical.

EXAMPLE 4

Presence of Subglutinol in T. Wilfordii Extracts

Tripterygium wilfordii plants were obtained in Taiwan. Plants were air dried in sunlight. The root xylem of the plants (g) was ground into a crude powder and extracted with 5 volumes (on a ml/g basis relative to the mass of the crude powder) of 95% ethanol, under reflux at 85° C. for 4 hours. The filtered xylem powder was then extracted two more times in 3 volumes (900 ml total) of 95% ethanol. The three extracts (total of about 3.3 L) were combined and the resulting mixture was concentrated at 50° C. under vacuum, to about 2% of the original volume, i.e., about 66 ml. The ethanol extract syrup obtained was then diluted with 33 ml water, and filtered through Whatman #1 filter paper. The filtrate was extracted 4 times (50 ml/extraction) with methylene chloride. The combined filtrate (about 200 ml) was concentrated.

The plant extract was chromatographed by TLC as described in Example 3. The region on the TLC plates containing a UV-absorbing spot (254 nm) and also reacting with 1% vanillin sulfuric acid was scraped from the plate and eluted with acetonitrile. Subsequently, the residue was respotted on a clean plate and again separated by TLC chromatography. The relative $R_F$ values of the compound from the TW plant were compared with the authentic subglutinol purified from Fusarium spp and found to be the same.

In addition, the sample from the plant and the subglutinol purified from the Fusarium spp were subjected to electrospray mass spectrometry. Both samples yielded virtually identical mass spectra, each having a parent ion (M+Na$^+$) at 449 mass units. The amount of subglutinol in the plant extract is estimated to be less than 0.1% of the total organic solvent extract. By contrast, the amount obtainable from the fungal extract is about 6.5 mg/L culture, corresponding to roughly 0.2% of total fungal cell mass.

EXAMPLE 5

Suppression of PBL Proliferation in Vitro

This example examines the ability of subglutinol to suppress the proliferation of human peripheral blood lymphocytes (PBLs) when stimulated with X-35 (AMAC #0178), an anti-CD3 surface antigen antibody. Human PBLs were prepared using an established method (Boyum). Human blood buffy coat samples, approximately 25 ml/donor, were obtained from the Stanford University Medical Center Blood Bank. Using sterile technique, the buffy coat samples were gently resuspended in a total volume of 100 ml with the addition of calcium and magnesium free Hank's balanced salt solution (HBSS, Gibco, Grand Island, N.Y.) at room temperature. A volume of 25 ml of the cell suspension was then layered onto 15 ml of Ficoll-Pacque (Pharmacia LKB Biotechnology, Uppsala, Sweden) in a 50 ml conical centrifuge tube. Tubes were centrifuged in a Beckman GPR tabletop centrifuge (GH-3.7 Rotor) at 400×g for 30 minutes at 15° C. Following centrifugation, the PBL suspensions at the interfaces were transferred to new 50 ml tubes using a transfer pipette, and the PBL samples were resuspended in a total volume of 45 ml HBSS and centrifuged at 354×g for 10 minutes at 15° C. Supernatants were discarded. The cell pellets were suspended in 10 ml HBSS, combined to make a total of 45 ml HBSS, and centrifuged at 265×g for 10 minutes at 15° C. The cell pellets were suspended in 10 ml of X-Vivo tissue culture medium (BioWhittakar, Walkersville, Md) and counted using a hemocytometer. Tissue culture medium was then added to achieve a final cell concentration of 1×10$^6$ cells/ml.

Assays were carried out in round-bottom 96 well microliter tissue culture plates (Costar #3790, Cambridge, Me.). PBLs from 2 different donors were used in parallel in all experiments. A volume of 100 µl PBL suspension was added to each well using a multichannel pipette. X-35 was added 25 µl per well to give a final concentration of 5 ng/ml to stimulate PBL proliferation. Subglutinol was dissolved in DMSO (10 mg/ml) and then diluted in sterile X-Vivo tissue culture medium. Samples were added 25 µl per well to obtain the final concentrations between 1 and 20 µg/ml. Wells with X-35 only or medium alone served as controls. The total volume for each well was 150 µl.

Plates were incubated at 37° C. in a 7% CO$_2$ incubator for 72 hours. During the last four hours of incubation, 50 µl of X-Vivo medium containing 0.5 µCi [$^3$H] Thymidine (Amersham, 49 Ci/mmol, Arlington Heights, Ill.) was added to each well. Cells were harvested onto filtermat using a cell harvester (Harvester 96, Tomtec). The filtermat was dried for 30 minutes under a heat lamp and then put into a sample bag. Beta Plate Scint (Pharmacia LKB Biotechnology; 10 ml) was added to the bag and sealed with Heat sealer (Pharmacia LKB Biotechnology). Samples were counted in a liquid scintillation counter (1205 Betaplate, Pharmacia LKB Biotechnology). The following formula was used to calculate % suppression:

suppression of PBL proliferation =

(X35 control − sample)/(X35 control − medium control) × 100

The results are shown in FIG. 10, discussed above.

EXAMPLE 6

Inhibition of IL-I Action on Mouse Thymocytes

Mouse thymocytes were prepared, and the action of IL-1, which stimulates thymocyte proliferation, was measured using standard techniques (O'Gara, 1990). Three to six week old C3H/HeN male mice (Simonson Laboratory, Gilroy, Calif.) were sacrificed by CO$_2$ inhalation. Thymi were removed, separated from adherent non-thymic tissue, homogenized in Hank's balanced salt solution (HBSS, Gibco) using a glass homogenizer, and centrifuged at 200×g for 10 minutes at 15° C. Following an additional wash in HBSS, the thymocytes were resuspended in RPMI 1640 medium (Gibco) containing 50 µM 2-mercaptoethanol, 2 mM glutamine, 1 mM sodium pyruvate, non-essential amino acids 100 U/ml penicillin, 100 µg/ml streptomycin and 10% heat-inactivated fetal bovine serum. Cells were cultured in round-bottom 96 well microtitre tissue culture plate (Costar #3799), 6×10$^5$ cells per well in a volume of 100 µl. Recombinant human IL-1β (R&D Systems #201-LB) together with phytohemagglutinin A (PHA, Pharmacia) were added to the cells in a volume of 25 µl per well to give final concentrations of 0.08 ng/ml and 10 µg/ml respectively. Subglutinol was dissolved in DMSO (10 mg/ml), then diluted with culture medium to various concentrations.

Subglutinol was added, 25 µl per well, to obtain final concentrations of subglutinol between 0.001 and 0.78 µg/ml. Wells with PHA and rIL-1 only or PHA or medium alone served as controls. Total volume for each well was 150 µl. Plates were incubated at 37° C., in a 5% CO$_2$ incubator for 72 hours. During the last four hours of incubation, 50 µl of medium containing 0.5 µCi [$^3$H] Thymidine (Amersham, 49

Ci/mmol) was added to each well. Cells were harvested and counted as above. Untreated cells (with medium alone) showed minimal thymidine incorporation. PHA alone stimulated thymidine incorporation 3–5 fold. Treatment with rIL-I plus PHA resulted in a more than 100-fold increase. The following formula was used to calculate % of suppression:

% suppression of IL-1 activity=(1-sample/(rIL-1+PHA control)× 100

The results are shown in FIG. 11.

EXAMPLE 7

Murine Mixed Lymphocyte Reaction

The mixed lymphocyte reaction described below is designed to test a drug's effect on suppression of the proliferation of lymphocytes in response to stimulation by irradiated allogeneic lymphocytes.

The responder cells (R) used were spleen cells from female C57BU6 mice. The stimulator cells (S) were spleen cells from female Balb/C mice 6 to 8 weeks of age (Jackson, Bar Harbor, Maine). The spleens were then removed from the mice and placed into 10 ml cold HBSS in a sterile petri dish. The spleen was then cut in half and gently smashed with two sterile frosted end of microslides. The cell suspension was then filtered through a sterile nylon mesh (Nytex, Tetco #HD-3-85) into a 15 ml conical polypropylene centrifuge tube. The cells were centrifuged at 200×g for 10 minutes in a Beckman GPR tabletop centrifuge (GH-3.7 Rotor).

Following an additional wash in HBSS, the spleen cells were resuspended in RPMI 1640 medium (Gibco) containing 50 µM 2-mercaptoethanol, 2 mM glutamine, 100 U/ml penicillin, 100 µg/ml streptomycin and 10% heat-inactivated fetal bovine serum.

The stimulator cells and part of the responder cells were diluted as $10 \times 10^6$ cells/ml and irradiated at 2000 rad with a Cesium Irradiator (Department of Radiation Oncology, Stanford University, Calif.) to inhibit proliferation. The irradiated cells were washed once to remove any toxic free radicals and their products resulting from irradiation. The responder cells (R), irradiated stimulator cells (Sx), and irradiated responder cells (Rx) were all diluted to $4 \times 10^6$ cells/ml.

In the assay, $4 \times 10^5$ R were cocultured with $4 \times 10^5$ Sx in 200 µl of medium in round-bottom 96 well tissue culture plate. Subglutinol, 50 µl at various concentrations, was added to the cells. The wells receiving no test samples show maximum proliferation.

Several controls were conducted in the MLR assay. The irradiated responder cells (Rx) were also added to the responder cells with or without the test samples. Rx or Sx alone was checked to make sure no proliferation occurred after irradiation. The spontaneous proliferation of R was also measured. The culture plates were incubated at 37° C., in a 5% $CO_2$ incubator for four days. The cells were labeled with 1 µCi of [$^3$H] Thymidine (Amersham, 49 Ci/mmol) in 20 µl of medium for the last 18 hours. Cells were harvested and counted as above.

The following formula was used to calculate % of suppression:

% suppression of MLR activity = {1 − [(R +

-continued

Sx + sample) − (R + Rx + sample)]/[(R + Sx) − (R + Rx)]} × 100

The results are shown in FIG. 12, discussed above.

EXAMPLE 8

Evaluation of Potential Toxicity (MTT Assay)

Potential cytotoxicities of test samples were assessed by measuring the effect of subglutinol on the reduction of MTT (3-[4,5-Dimethylthiazole-2-yl]-2,5-diphenyl-tetrazolium bromide) by cultured cells. MTT, a yellow-colored compound, is reduced by mitochondrial enzymes to form a purple crystalline reduction product, formazane, providing an index of cellular respiration as well as a sensitive assay for cytotoxicity (Green, 1984).

Cytotoxicity was assessed in cultured human PBLs. A stock solution of MTT (Sigma, St. Louis, Mo.), 5 mg/ml phosphate buffered saline, pH 7.4, was prepared and stored in the dark at 4° C. PBLs were cultured with various concentrations of test samples in flat-bottom 96 well tissue culture plate (Costar #3595) using the same conditions as in Example 5 above, except that X-35 was replaced with the appropriate medium.

Untreated cells in medium alone were used as controls in each experiment. Following 21 hours of incubation of cells, 25 µl of MTT solution was added to each well. After an additional three hour incubation, the experiment was terminated by adding a solution of 10% sodium dodecyl sulfate in 0.01 N HCl.

Following overnight incubation at 37° C. (to solubilize the formazane crystals), optical density was determined at 570–650 nm in a microplate reader (Thermo max, Molecular Devices, Calif.). Data are expressed as % cytotoxicity. Subglutinol concentrations of 0.03, 0.1, and 0.3 µg/ml gave % cytotoxicity values of 0, 20, and 28%, respectively.

Although the invention has been described with respect to particular methods and applications, it will be appreciated that various changes and modifications may be made without departing from the spirit of the invention.

It is claimed:

1. A compound having the structure:

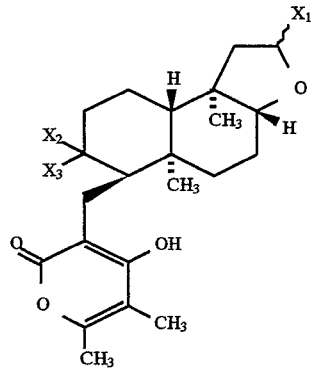

or a mirror image thereof, wherein $X_1$ is 2,2-dimethylvinyl and $X_2$ and $X_3$ together are =$CH_2$; or $X_1$ is 2,2-dimethyloxiranyl, and $X_2$ and $X_3$ together are —O—$CH_2$—; or $X_1$ is 1,2-dihydroxy-2-methyl-propyl, $X_2$ is —$CH_2OH$, and $X_3$ is OH; or $X_1$ is 2-hydroxy-2-methylpropyl, $X_2$ is H, and $X_3$ is $CH_2OH$; or $X_1$ is COOR, and $X_2$ and $X_3$ together are =O, where R is a lower alkyl, phenyl, or benzyl group; or $X_1$ is 2-methylpropyl, $X_2$ is H, and $X_3$ is $CH_3$.

2. A compound in accordance with claim 1, wherein $X_1$ is 2,2-dimethylvinyl and $X_2$ and $X_3$ together are $=CH_2$.

3. A compound in accordance with claim 1, wherein $X_1$ is 2,2-dimethyloxiranyl, and $X_2$ and $X_3$ together are $-O-CH_2-$.

4. A compound in accordance with claim 1, wherein $X_1$ is 1,2-dihydroxy-2-methylpropyl, $X_2$ is $-CH_2OH$, and $X_3$ is OH.

5. A compound in accordance with claim 1, wherein $X_1$ is 2-hydroxy-2-methylpropyl, $X_2$ is H, and $X_3$ is $CH_2OH$.

6. A compound in accordance with claim 1, wherein $X_1$ is COOR, and $X_2$ and $X_3$ together are $=O$, where R is a lower alkyl, phenyl, or benzyl group.

7. A compound in accordance with claim 1, wherein $X_1$ is 2-methylpropyl, $X_2$ is H, and $X_3$ is $CH_3$.

8. A compound in accordance with claim 1, consisting essentially of the 12-(R) stereoisomer.

9. A compound in accordance with claim 1, consisting essentially of the 12-(S) stereoisomer.

10. A compound in accordance with claim 1, wherein the compound is radiolabeled with $^{14}C$.

11. A pharmaceutical composition for use in immunosuppression therapy, comprising a compound in accordance with claim 1 in a pharmaceutically acceptable vehicle.

* * * * *